United States Patent [19]

Harada et al.

[11] 4,309,385
[45] Jan. 5, 1982

[54] APPARATUS FOR MEASURING VOLATILE HYDRIDES

[75] Inventors: Hikaru Harada, Kamakura; Teruo Akiyama; Tuneo Hiyama, both of Tokyo, all of Japan

[73] Assignee: Nippon Sanso K.K., Tokyo, Japan

[21] Appl. No.: 109,329

[22] Filed: Jan. 4, 1980

[30] Foreign Application Priority Data

Jan. 26, 1979 [JP] Japan ................................. 54-8027
Jan. 26, 1979 [JP] Japan ................................. 54-8262

[51] Int. Cl.³ .......................................... G01N 21/00
[52] U.S. Cl. .................................. 422/83; 23/232 E; 23/230 PC; 422/78; 422/80
[58] Field of Search ................ 422/62, 78, 80, 98, 422/83; 23/232 E

[56] References Cited
U.S. PATENT DOCUMENTS

| | | | |
|---|---|---|---|
| 3,748,097 | 7/1973 | Lerner | 23/232 E |
| 3,788,124 | 1/1974 | Teton | 23/232 E X |
| 3,826,614 | 7/1974 | Capuano | 422/78 |
| 3,844,719 | 10/1974 | Hammitt | 422/78 |
| 4,023,929 | 5/1977 | Becker et al. | 422/78 |
| 4,049,383 | 9/1977 | Burton et al. | 23/232 E |

*Primary Examiner*—Michael S. Marcus
*Attorney, Agent, or Firm*—Darby & Darby

[57] ABSTRACT

According to the present invention volatile hydrides such as diborane, arsine, phosphine and the like are made to react with mercuric oxide at an ordinary temperature to produce mercury atoms, the concentration of which is thereafter measured and the concentration of volatile hydrides is determined in accordance with the corresponding measured mercury atom concentration. As the measuring apparatus according to the present invention is made to measure mercury atoms, it can easily detect even extremely small quantity of substances such as volatile hydrides and respond quickly, thus enabling the apparatus being suitably used as a monitor in the semiconductor industry.

19 Claims, 2 Drawing Figures

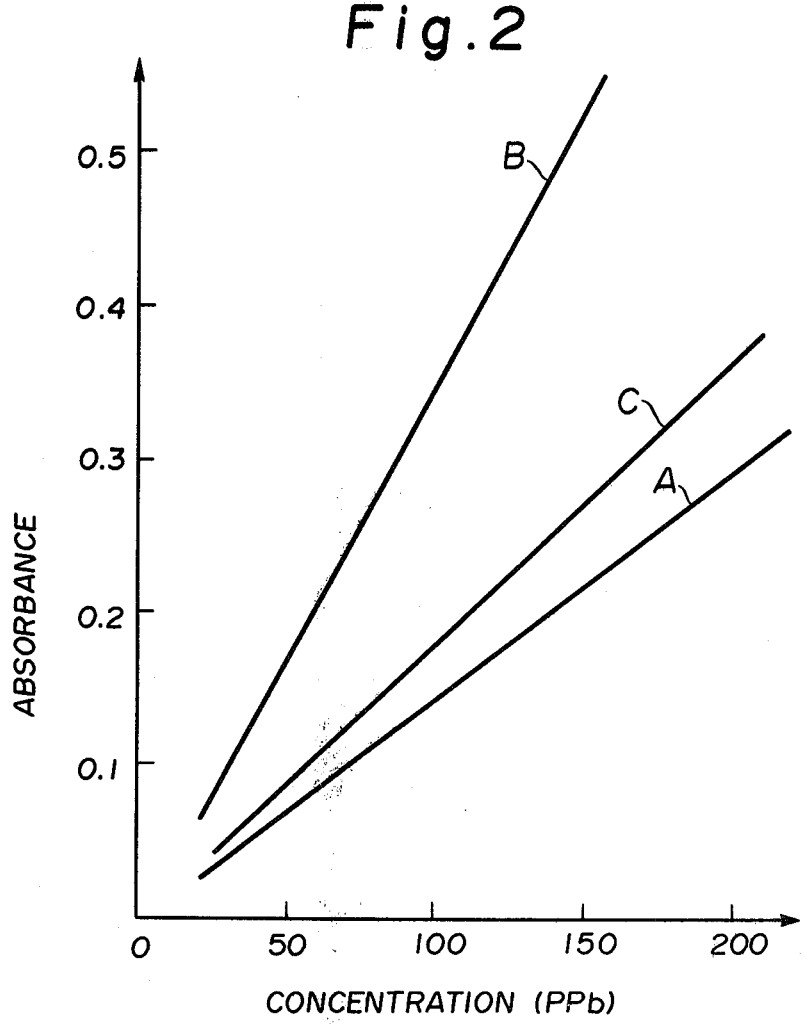

APPARATUS FOR MEASURING VOLATILE HYDRIDES

BACKGROUND OF THE INVENTION

The present invention relates to an apparatus for measuring such volatile hydrides as diborane ($B_2H_6$), arsine ($AsH_3$), phosphine ($PH_3$), stibine ($SbH_3$), hydrogen selenide ($SeH_2$), monosilane ($SiH_4$) and the like which are broadly used as doping material or epitaxializer in the field of semiconductor industry.

Hitherto, there have been known methods for measuring the volatile hydride; (1) colorimetric methods (methods of chemical analysis) based primarily upon their reaction with reagents, (2) infrared methods utilizing the property of the gas molecule to be examined to absorb the infrared rays, (3) ultraviolet methods utilizing the property of the gas molecule to be examined to absorb the ultraviolet rays, and (4) atomic absorption method based on measuring the light absorption of the atomic molecule caused by thermal decomposition of the gas to be examined. However, colorimetric methods have such weak points as that the measuring operation thereof is not only complicated but also time consuming. In case of infrared and ultraviolet methods, both of them proved to have poor measurement sensitivity and even concentrations as high as several ppm were hard to be measured by these methods. Further, in the case of atomic absorption method various inconveniences have been experienced; for examples, high temperature on the frame was unavoidable, such apparatus was expensive and the like. As mentioned above none of hitherto known methods for measuring volatile hydrides could bring about a satisfactory result. Further, it has been considered to be extremely difficult or almost impossible to determine extremely small quantities of hydrides by hitherto known method. These compounds being strongly toxic, and the threshold limit value or permissible concentration is generally considered to be as small as about 0.1 ppm, for example; 0.05-0.3 ppm (50-300 ppb), for arsine 0.05 ppm, for phosphine 0.3 ppm, for stibine 0.1 ppm, for hydrogen selenide 0.05 ppm, and for diborane 0.1 ppm, respectively. These compounds were difficult to be detected and measured with accuracy. Especially, diborane has been considered heretofore almost impossible to measure. In view of the fact that volatile hydrides are broadly used these days, the above situation was not desirable for health maintenance.

SUMMARY OF THE INVENTION

It is an object of the present invention to provide an apparatus for measuring volatile hydrides in which even extremely small quantities of hydrides which have hitherto been deemed either difficult or almost impossible to be determined, can be easily and accurately measured. Another object of the invention is to provide an apparatus for carrying out said measurement which can be operated in a simple manner and effect measurement in a short period of time and is yet inexpensive because of dispensing with the high temperature heating part. The apparatus of the present invention is hence suitable for industrial use. The first characteristic according to the present invention is that volatile hydrides are made to react with mercuric oxide to produce atomic mercury, the concentration of the mercury atom is thereafter measured and the concentration of volatile hydrides is determined in accordance with corresponding concentration of mercury atom. The present invention is characterized by a measuring apparatus comprising a reactor part, in which volatile hydrides are made to react with mercuric oxide and the mercuric oxide is thereby converted to atomic mercury, and a detection part in which the mercury atom produced by this reaction is inspected of its concentration by ultraviolet spectroscopic analysis.

DETAILED DESCRIPTION OF THE INVENTION

Figure 1:
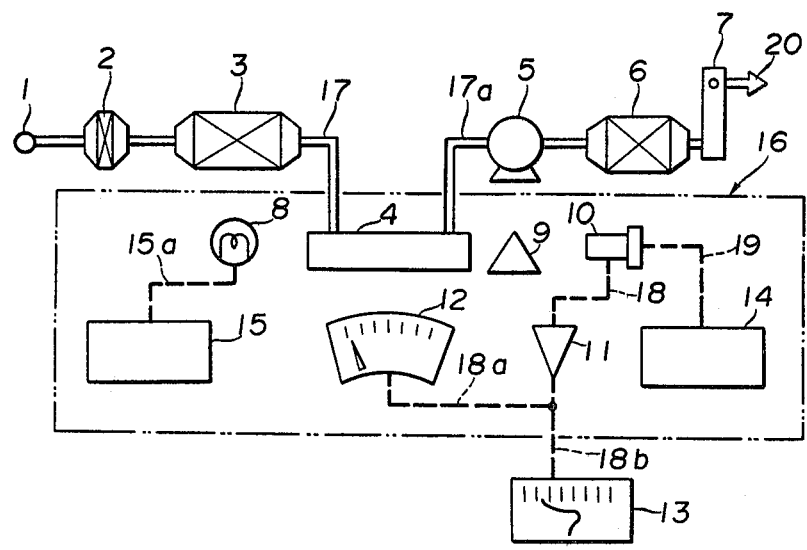

To begin with, volatile hydrides such as diborane, arsine, phosphine, stibine, hydrogen selenide and monosilane contained in inert gas like nitrogen or in air are made to react with a stoichiometric excess of mercuric oxide at an ordinary temperature, the mercuric oxide being thereby converted to atomic mercury. The reactions between volatile hydrides above mentioned are considered to proceed with in accordance with the following schemes:

$$B_2H_6 + 3H_gO \rightarrow 3H_g + 3H_2O + 2B \quad (1)$$

$$2A_sH_3 + 3H_gO \rightarrow 3H_g + 3H_2O + 2A_s \quad (2)$$

$$2PH_3 + 3H_gO \rightarrow 3H_g + 3H_2O + 2P \quad (3)$$

$$2S_bH_3 + 3H_gO \rightarrow 3H_g + 3H_2O + 2S_b \quad (4)$$

$$S_eH_2 + H_gO \rightarrow H_g + H_2O + S_e \quad (5)$$

$$S_iH_4 + 2H_gO \rightarrow 2H_g + 2H_2O + S_i \quad (6)$$

Then, the concentration of the mercury atom generated through these reactions is in proportion to the concentration of volatile hydrides and measured by means of ultraviolet spectroscopic analysis and the concentration of volatile hydrides is thereby determined by comparing the corresponding concentration of measured mercury atom. As mercury atom is easily detected even in a extremely small quantity, detection of volatile hydrides can be easily performed. Further, as shown in the above formulas (1)-(6), except in case of hydrogen selenide, 1 mole thereof produces only 1 mole of mercury atom, 1 mol of diborane produces 3 mols of mercury atom and in case of monosilane 1 mol thereof produces 2 mols of mercury atom and further in case of arsine, phosphine and stibine each 1 mol thereof produces 1.5 mols of mercury atom. In case of subject gases other than those including hydrogen selenide, the mercury atom generated per 1 mol of volatile hydrides amounts to 1.5-3 mols, thus making it possible for these hydrides to be detected and determined with high sensitivity. By recording and indicating the data obtained through detection as mentioned above, the concentration of volatile hydrides is determined easily and accurately.

FIG. 2 is a diagram of the relations between absorbances of mercury atoms and concentrations of diborane, arsine and phosphine found by experiment. First, plural samples with known mercury atom concentrations were prepared and then absorbance of mercury atom were measured on each of them by means of ultraviolet absorption method and the results such obtained were plotted. Consequently, a calibration curve was obtained as illustrated by curve A.

On the other hand, plural samples with known concentration were prepared beforehand for diborane, arsine and phosphine respectively and made to react with mercuric oxide. Absorbances of obtained mercury atoms were measured and plotted respectively. Consequently, Curve B was obtained for diborane and Curve C for arsine or phosphine. Comparing Curves A, B and C illustrated in FIG. 2 with one another, it was found that in case of diborane 1 mol thereof produced about 3 moles of mercury atom, while in case of arsine or phosphine 1 mol thereof produced about 1.5 mols of mercury atom. By this way, it was confirmed that reactions were actually proceeded with according to the above schemes (1)–(3).

Next, samples containing diborane, arsine and phosphine with unknown concentrations of a rank as low as ppb were made to react with mercuric oxide respectively and the absorbance of thereby produced mercury atoms was measured by means of an ultraviolet absorption method, and based on the obtained absorbance mercury atom concentrations the concentration of the hydrides were found by the help of Curve A. Then, the concentration of diborane was calculated by multiplying $\frac{1}{3}$ to the atomic mercury concentration and those of arsine and phosphine by $\frac{2}{3}$ respectively. It was thus confirmed that even concentrations as low as ppb can be measured easily and accurately. In the above embodiment mercury atoms were measured by means of ultraviolet absorption method. As a matter of course, however, the above embodiment was an example and other measuring methods may also be employed.

Now, an embodiment of the apparatus according to the present invention will be explained in detail by referring to FIG. 1.

The measuring apparatus of the present invention comprises a sample introducing part into which samples containing volatile hydride such as diborane, arsine, phosphine, stibine, hydrogen selenide or monosilane in an inert gas like nitrogen and air are introduced, a reaction part in which volatile hydrides are made to react with mercuric oxide thereby converting the mercuric oxide to mercury atom, a detection part in which the mercury atom concentration generated in the reaction part is detected by ultraviolet absorption method, an indicating and recording part in which the mercury atom concentration detected in the detection part is indicated and recorded and the concentrations of volatile hydrides are determined corresponding to the mercury atom concentration, and a discharge part in which the already detected gases inclusive of atomic mercury are discharged after removal of poison.

Said sample introducing part is composed of a gas entrance 1 and a dust eliminator 2 which is connected by way of duct 17 to the gas entrance 1. Said reaction part comprises of mercuric oxide reaction cell 3 which is connected to said dust eliminator 2 by way of gas duct 17 and is filled with pulverulent mercuric oxide. Further, said detection part, being an apparatus known as an atomic absorption analyzer 16, comprises a light absorption cell (quartz window) 4 connected to said mercuric oxide reaction cell 3 by way of gas duct 17, an ultraviolet radiation source 8, such as mercury low voltage discharge lamp or mercury hollow cathode lamp, for the purpose of radiating ultraviolet rays into this light absorption cell 4, a power supply 15 connected to said ultraviolet radiation source 8 by way of a power supply circuit 15a, a wave length selector 9 such as monochrometer (diffraction grating) or interference filter, a light receiver bulb 10 such as electron multiplier tube, a photo-electric tube and photo-electric element and a high voltage power supply 14 connected to said light receiver bulb 10 by way of a power supply circuit 19.

Further, the aforesaid indicating and recording part comprises a signal operation amplifier 11 connected to said light receiver bulb 10 by way of an electric signal circuit 18, a concentration index gauge 12 connected to the signal operation amplifier 11 by way of an electric signal circuit 18a and an indicating and recording gauge 13 connected to the same amplifier 11 by way of another electric signal circuit 18b which branches from said electric signal circuit 18a.

Further, the above mentioned discharge part comprises of a gas-pump 5, a depoisoner 6, a flowmeter 7 and a gas-exit 20, all being incorporated in a gas passage 17a that derives from said light absorption cell 4.

Now, working order of the measuring apparatus according to the present invention will be described hereunder.

To begin with, gaseous sample containing volatile hydrides as mixed with an inert gas like nitrogen or with air is introduced from the gas entrance 1 and is led into the mercuric oxide reaction cell 3 after being made free of dust in the dust eliminator 2. Volatile hydrides in the sample gas thus introduced into the reaction cell 3 are made to react with the mercuric oxide filled up in the inner space of the cell 3 and the mercury oxide is thereby converted to mercury atom. Next, the sample gas which contains vaporous mercury atom generated in the cell 3 is transferred via the gas duct 17 to the light absorption cell (quartz window) 4. Activating the ultraviolet radiation source 8 by the help of the power supply 15, ultraviolet rays are radiated into the light absorption cell 4 and after received by the wave length selector 9 are received in the light receiver bulb 10 which is operated by the high voltage power supply 14. The signal coming through the electric signal circuit 18 is amplified by the signal operation amplifier 11 and the amplified signal is put into the concentration index gauge 12 via the electric signal circuit 18a while the signal is also put into the indicating and recording gauge 13 by way of electric signal circuits 18a and 18b. In addition, the gas passes through said light absorption cell 4 and is transferred by actuating the gas-pump 5 from the gas passage 17a to depoisoner 6 and after being depoisoned therein the gas is discharged from the gas exit 20.

The mercury concentration indicated in the concentration index gauge through an operation as described above is multiplied by $\frac{1}{3}$, for example, in case of diborane and $\frac{2}{3}$ in case of arsine and phosphine in accordance with the above reaction schemes or diagram in FIG. 2, and each answer such obtained is the concentration of these volatile hydrides. When the measuring substance in sample gas is specified, the scales of the concentration index gauge 12 and the indicating and recording gauge 13 may be adequately adjusted beforehand so that the concentration of volatile hydride can be obtained immediately.

Further, although in the above description explanations are given about the case of measuring gaseous hydrides, it is a matter of course that also powders and solutions of such metals as As and Pb which are convertible into volatile hydride by means of a proper apparatus, such as a reductive vaporizer can likewise be detected and measured.

As explained hereinbefore about the present invention volatile hydrides react with mercuric oxide so as to produce mercury atom, the concentration of volatile hydride is determined in accordance with corresponding to the measured mercury atom concentration. As for mercury atom, even very small quantity can be detected easily. In addition to this, where most of the volatile hydrides are reacted with mercuric oxide, 1 mole of the hydride produces 1.5 to 3 moles of mercury atom. Therefore, the measurement can be carried out with so high sensitivity that even an extremely small quantities such as the threshold limit value can be detected and determined easily and accurately. The present invention is advantageous further in that the measurement can be carried out at ordinary temperatures and by a simple operation and in a short time. Further, the apparatus according to the invention is a suitable gauge to be used in industry, because it is a monitor with high sensitivity good for the purpose of securing health of workers and maintaining safety of environment in the field of semiconductor industry or the like where volatile hydrides are handled. In addition, the price of the apparatus is moderate, especially with respect to diborane, since no practical apparatus has been provided for measuring very small quantities of volatile metallic hydrides, the present invention will render a significant effect on to industries concerned. When the apparatus is used as monitor, the aforementioned concentration index gauge 12 and indicating and recording gauge 13 are unnecessary and it may well be so constructed as to generate signal when the concentration of hydrides is detected to be more than threshold limit value and send the signal directly to an alarm circuit. Further, it is recommendable to use a mercury low voltage discharge lamp as ultraviolet radiation source, an interference filter as wave length selector and a photo-electric tube or photo-electric element as light receiver bulb for a low priced apparatus.

What is claimed is:

1. An apparatus for measuring the concentration of volatile hydrides in a gas sample which comprises:
   a reactor containing mercuric oxide wherein the volatile hydrides react stoichiometrically with said mercuric oxide to form mercury atom gas and reacted hydrides,
   means for transferring the gas sample to said reactor,
   means for conducting said mercury atom gas and said reacted hydrides to a detection means,
   said detection means comprising an ultraviolet radiation source, an ultraviolet absorption cell for absorbing ultraviolet radiation, and a light detector for detecting ultraviolet light transmitted through said cell, said transmitted light being directly related to the concentration of said mercury atom gas, and said detection means being operative at room temperature, and
   means for indicating and recording the concentration of said volatile hydrides in the gas sample.

2. An apparatus for measuring the concentration of volatile hydrides in a gas sample as set forth in claim 1 wherein said gas sample comprises at least one gas selected from the group consisting of diborane, arsine, phosphine, stibine, hydrogen selenide, monosilane and lead.

3. An apparatus for measuring the concentration of volatile hydrides as set forth in claim 2 wherein said conversion means comprises an indicating and recording device which receives an electric signal from said detection means for indicating and recording the concentration of the volatile hydrides in the gas sample.

4. An apparatus for measuring the concentration of volatile hydrides in a gas sample as set forth in claim 2 which comprises an alarm circuit activated by an electric signal from said detection means.

5. The apparatus of claim 1 including a filter interposed between said cell and said light detector.

6. The apparatus of claim 5 which comprises a discharge passage interconnected with said absorption cell, and a gas pump connected to said passage for withdrawing gaseous products from said cell.

7. The apparatus of claim 6 further comprising means for removing toxic products from said gaseous products, said means being interconnected with said pump.

8. The apparatus of claim 7 wherein said means for indicating and recording comprise a concentration index gauge interconnected with said light detector and an indicating and recording gauge interconnected with said light detector.

9. The apparatus of claim 8 further comprising apparatus for detecting a signal from said light detector, said signal being transmitted to said gauges.

10. An apparatus for measuring the concentration of volatile hydrides in a gas sample which comprises:
    a reactor containing mercuric oxide wherein the volatile hydrides react stoichiometrically with said mercuric oxide to form vaporous mercury atom and other reacted products,
    means for transferring the gas sample to said reactor,
    means for conducting said vaporous mercury atom to a detection means,
    said detection means comprising an ultraviolet radiation source, an ultraviolet absorption cell for absorbing ultraviolet radiation, and a light detector for detecting ultraviolet light transmitted through said cell, said transmitted light being directly related to the concentration of said vaporous mercury atom, and
    conversion means for indicating, recording and/or alarming in response to a signal from said detection means.

11. An apparatus for measuring the concentration of volatile hydrides in a gas sample as set forth in claim 10, wherein said detection means is operative at room temperature.

12. An apparatus for measuring the concentration of volatile hydrides in a gas sample as set forth in claim 11, wherein said gas sample comprises at least one gas selected from the group consisting of diborane, arsine, phosphine, stibine, hydrogen selenide, monosilane and lead.

13. An apparatus for measuring the concentration of volatile hydrides as set forth in claim 10 wherein said conversion means comprises an indicating and recording device which receives an electric signal from said detection means for indicating and recording the concentration of the volatile hydrides in the gas sample.

14. An apparatus for measuring the concentration of volatile hydrides in a gas sample as set forth in claim 10 which comprises an alarm circuit activated by an electric signal from said detection means when volatile hydrides in sample gas are detected or when amounts in excess of a predetermined value thereof are detected.

15. The apparatus of claim 10 including a wave length selector interposed between said cell and said light detector.

16. The apparatus of claim 15 which comprises a discharge passage interconnected with said absorption cell, and a gas pump connected to said passage for withdrawing gaseous products from said cell.

17. The apparatus of claim 16 further comprising means for removing toxic products from said gaseous products, said means being interconnected with said pump.

18. The apparatus of claim 17 wherein said means for indicating and recording comprise a concentration index gauge interconnected with said light detector and an indicating and recording gauge interconnected with said light detector.

19. The apparatus of claim 18 further comprising apparatus for detecting a signal from said light detector, said signal being transmitted to said gauges.

* * * * *